United States Patent
Biava et al.

(10) Patent No.: US 10,937,921 B2
(45) Date of Patent: Mar. 2, 2021

(54) METHOD FOR MANUFACTURING A SENSOR CHIP FOR THE DIRECT CONVERSION OF X-RAYS, A SENSOR FOR THE DIRECT CONVERSION OF X-RAYS AND THE DENTAL RADIOLOGY APPARATUS FOR USING SUCH A SENSOR

(75) Inventors: Dominique Biava, Croissy-Beaubourg (FR); Mathieu Rault, Croissy-Beaubourg (FR); Jean-Marc Inglese, Bussy Saint Georges (FR); Sylvie Bothorel, Paris (FR); Didier Gourier, Paris (FR); Laurent Binet, Vitry-sur-Seine (FR); Philippe Barboux, L'Hay les Roses (FR); Jean-Pierre Ponpon, Eckbolsheim (FR)

(73) Assignee: TROPHY, Croissy-Beaubourg (FR)

( * ) Notice: Subject to any disclaimer, the term of this patent is extended or adjusted under 35 U.S.C. 154(b) by 687 days.

(21) Appl. No.: 14/408,368

(22) PCT Filed: Jun. 21, 2012

(86) PCT No.: PCT/FR2012/051402
§ 371 (c)(1),
(2), (4) Date: Dec. 16, 2014

(87) PCT Pub. No.: WO2013/190187
PCT Pub. Date: Dec. 27, 2013

(65) Prior Publication Data
US 2015/0155421 A1 Jun. 4, 2015

(51) Int. Cl.
*H01L 31/18* (2006.01)
*H01L 31/08* (2006.01)
(Continued)

(52) U.S. Cl.
CPC ............... *H01L 31/18* (2013.01); *A61B 6/14* (2013.01); *A61B 6/145* (2013.01); *H01L 31/0368* (2013.01); *H01L 31/085* (2013.01)

(58) Field of Classification Search
CPC .. H04N 5/32; G01T 1/202; G01T 1/20; A61B 6/4241
See application file for complete search history.

(56) References Cited

U.S. PATENT DOCUMENTS 5,892,227 A * 4/1999 Schieber ................... G01T 1/24
250/370.12
2002/0039272 A1* 4/2002 Mizuno ............... C04B 35/4682
361/311

FOREIGN PATENT DOCUMENTS

CN 1167529 A 12/1997

OTHER PUBLICATIONS

International Search Report, dated Jun. 21, 2012, International Application No. PCT/FR2012/051402, 4 pages.
(Continued)

*Primary Examiner* — Hoon K Song

(57) ABSTRACT

This invention relates to a method to manufacture a chip to detect the direct conversion of X-rays. It also relates to a direct conversion detector for X-rays using such a chip and dental radiology equipment using at least one such detector. The method to manufacture the wafer comprises a step for applying pressure (3, 4, 4 *a*) to a powdered polycrystalline semiconductor material and a step for heating (5-9) during a set time period. It comprises a preliminary step for providing an impurity level of at least 0.2% in the polycrystalline semiconductor material.

13 Claims, 2 Drawing Sheets

(51) Int. Cl.
*A61B 6/14* (2006.01)
*H01L 31/0368* (2006.01)

(56) References Cited

OTHER PUBLICATIONS

M. Schieber et al., "Theoretical and Experimental Sensitivity to X-rays of Single and Polycrystalline $HgI_2$ Compared with Different Single-Crystal Detectors", Nuclear Instruments and Methods in Physics Research, Section A 458, 2001, pp. 41-46.
R. Turchetta et al., "Imaging With Polycrystalline Mercuric Iodide Detectors Using VLSI Readout", Nuclear Instruments and Methods in Physics Research, Section A 428, 1999, pp. 88-94.
Schlesinger, T.E., and James, R.B., "Semiconductors for Room Temperature Nuclear Detector Applications", Semiconductors and Semimetals, vol. 43, Aug. 8, 1995, pp. 91-93.
Willig, W.R., "New Gamma Detectors of Mercury Iodide and Other Heavy Metal Compounds", Siemens Forsch.-u.Entwickl.-Ber. Bd. 2 (1973) Nr. 3, pp. 157-160.
Lamonds, H.A., "Review of Mercuric Iodide Development Program in Santa Barbara", EG&G Santa Barbara Operations, Jan. 1, 1982, S-197-TP, pp. 1-5.

\* cited by examiner

METHOD FOR MANUFACTURING A SENSOR CHIP FOR THE DIRECT CONVERSION OF X-RAYS, A SENSOR FOR THE DIRECT CONVERSION OF X-RAYS AND THE DENTAL RADIOLOGY APPARATUS FOR USING SUCH A SENSOR

CROSS REFERENCE TO RELATED APPLICATIONS

This application is a 371 national stage application of earlier filed international application Serial No. PCT/FR2012/51402, filed on 2012 Jun. 21, entitled "A METHOD FOR MANUFACTURING A SENSOR CHIP FOR THE DIRECT CONVERSION OF X-RAYS, A SENSOR FOR THE DIRECT CONVERSION OF X-RAYS AND THE DENTAL RADIOLOGY APPARATUS FOR USING SUCH A SENSOR", in the names of Dominique BIAVA, et al., which is incorporated herein in its entirety.

TECHNICAL FIELD OF THE INVENTION

This invention relates to a method to manufacture a chip from semiconductor material to detect the direct conversion of X-rays. It also relates to a direct conversion detector for X-rays using such a chip and a dental radiology apparatus using at least one such sensor.

STATE OF THE ART

In the prior art, radiological equipment has already been proposed, particularly dental, which makes it possible to obtain images in two or three dimensions (2D or 3D) from the inside of the mouth. An X-ray source is placed so that it may be linked to an X-ray detector in such a way that the image to be transmitted through the patient's head is formed on a given support in connection with the X-ray detector.

A first requirement specific to dental radiology, is that the amount of X-rays necessary for obtaining an image must be as low as possible. Indeed, high-dose X-rays may have a detrimental effect on health. Not only must the X-ray dose received by the patient be strictly reduced, but those parasitically received by the operator must also be reduced in accordance with the extremely strict international standards.

Among all the known X-ray detectors, a particular type of X-ray detectors known as a direct conversion X-ray detector appears.

While an indirect conversion detector has a scintillator whose role is to convert an X-photon received into a light photon, which is then converted into electric charges using a traditional photonic converter. The direct conversion detector directly transforms an X-ray photon received into electrical charges. These charges are then collected by applying an electrical field.

For this purpose, a direct conversion detector comprises a chip. This semiconductor chip produces an electric current due to the migration in an electrical field effect of the charges produced by absorption of an X-photon.

An object of this invention is to manufacture and put together the semiconductor material into a ceramic semiconductor wafer to carry out the direct detection of an X-photon flow into an electrical current for the purpose of creating a 2D or 3D image of a scene illuminated by an X-ray source.

However, in dental radiology, it is understood that several techniques require the special characteristics of direct conversion X-ray detectors. In fact, the production of panoramic radiographies disclose both dental arches fully and the production of images, especially by the OPG technique, require the ability to rapidly repeat several image acquisitions, and that the direct conversion X-ray detector must rapidly detect.

Another object of the invention is to manufacture a new chip for performing the direct conversion of several successive X-photons flows more quickly into at least one electrical current in order to achieve a sequence of images of a 2D scene by an illuminated X-ray source.

In fact, the direct conversion X-ray detectors produced by the prior art suffer from certain limitations related to the semiconductor material. Additionally, the current methods for obtaining the semiconductor material have certain disadvantages.

Ideally, the semiconductor material should be inexpensive and easy to make.

The hazardous risk involved in the steps for preparing certain semiconductor materials is an obstacle to their development, particularly for their use in X-ray detectors.

The material must be allow for the production of sufficiently large sensors.

The material should have low porosity, so that it does not decrease the absorption properties of the X-rays Furthermore, porosity constitutes a barrier to the movement of electrical charges and can be one of the causes for the capture and deterioration of these charges, thus deteriorating the electrical transport properties of the material.

The surface opposite the wafer made with such a material must be very uniform to facilitate placement of electrodes on both sides and to ensure a roughness which is low enough to ensure a homogeneous electrical field.

The material should have a composition as close as possible to the stoichiometry of $HgI_2$, which must be reproducible and constant throughout its volume. In fact, a deviation from the stoichiometry can generate a parasitic phase that will disrupt the lines of the electric field with consequences which affect the sharpness of the image and can create defects which can trap electrical charges and thus degrade the sensitivity of the detector.

Throughout the rest of this application, we will refer to detector sensitivity as the ratio between the output variable (quantity of electrical charges in Coulombs) and the input variable (signal flow of the ionizing X-photon energy, i.e., the input dose per surface unit in Grays×cm$^2$). The sensitivity of the detector may be expressed in relative sensitivity based on this.

Some semiconductor materials are anisotropic, such as mercury iodide $HgI_2$. These anisotropic materials have one or more characteristics that depend on the orientation of the material. In the case of mercury iodide, resistance to the movement of electrical charges is lower along the crystallographic axis "c". It is therefore important that the C axis be oriented in the direction of electrical conduction from the outer surface of the material to the sensor when the anisotropic semiconductor material is integrated into the detector.

Single CdTe or $HgI_2$ type crystals of are constituted by a single grain and therefore have zero porosity. Such material is nevertheless tedious and difficult to prepare. Production of thin wafers with clean contact surfaces from the single crystal rod is not economically feasible. The growth of $HgI_2$ layers can be performed on a CMOS-type semiconductor substrate with a vacuum deposition in vapor phase (PVD method). Mercury iodide vapor is brought to 90° C. and condenses on the cold substrate at 70° C. The advantages of such growth is that the semiconductor material is deposited directly on the substrate (electronic reading circuit), and that the C axis, oriented along the direction of the crystal growth, which is orthogonal to the substrate surface, and therefore this axis is oriented along the direction of easy conduction for the electrical charges in the operating mode of the sensor thus obtained.

Nevertheless, this method has numerous disadvantages. The preparatory mode poses certain hazardous risks to health since it involves handling mercury or HgI2 in its gaseous state. It is technically difficult to produce since it demands strictly controlled production under vacuum and the temperatures of the $HgI_2$ and the substrate are very precisely defined. The composition and stoichiometry are highly dependent on the temperature of the $HgI_2$ in the gaseous phase, and on the temperature of the substrate and the speed of the deposit. Finally, since the flatness of the substrate is not perfect with respect to the mesh size of the crystal, during the beginning of the growth, it may be disturbed in certain areas and prevent conduction to the semiconductor interface material/electrode.

A second method from the prior art for obtaining a single crystal semiconductor material such as $HgI_2$ comprises dissolving $HgI_2$ powder in a hot solvent. It is then cooled and the solvent is allowed to evaporate before harvesting the monocrystal. This method is easier to implement than the previous method, but it is not reproducible. It does not allow control over the size and shape of the monocrystal. In addition, the monocrystals thus produced have a poorly controlled purity and composition, a poor surface finish and dimensions of the order of a millimeter which make them incompatible with large-area detectors.

A third method of the prior art comprises mixing the powder of a semiconductor material such as $HgI_2$ with a polymeric binder (a method called "PIB"—"In Particle In Binder"). The polymer has adhesive properties which bind the $HgI_2$ grains together thus forming a rigid material. The advantages of this method are the ease of preparation and the possibility of easily gluing the material thus obtained onto the CMOS sensor. The inventors performed an analysis of the disadvantages of the polycrystal thus obtained. There remains a particularly high porosity between the grains of the semiconductor material and a dispersion of the orientation of axis C within the material in the case of an anisotropic semiconductor material.

A fourth method from the prior art is to prepare the semiconductor material by sintering. Sintering is a method for manufacturing ceramics by growing the grains and then welding them together with an energy input by heating a powder, generally previously compacted by pressing, without melting it. Under the effect of the heat, the grains are welded together by inter-diffusion of the material, which allows cohesion of the piece. However, this method does not make it possible to obtain a material with satisfactory electrical transport properties. In fact, the material thus obtained would be very porous and lacking the preferential axis C orientation.

In the International Application WO-A-00/68999 published on Nov. 16, 2000, a technique of the prior art is described in which a CdTe based ceramic is produced by sintering. A step is proposed prior to shaping the pellet before sintering by means of die compaction. This initial powder compaction is done before heating, and thus the sintering, and constitutes a simple way to shape the chip. This type of CdTe selection processing does not achieve the intended results of the invention.

In the U.S. Pat. No. 5,892,227 (also published as International Application number WO-A 96/10194 dated Apr. 4, 1996) along with two other deposition techniques, (suspension and vapor deposition), a powder sintering technique is described for a semiconductor product or a mixture of semiconductor products. Setting the temperature in the furnace is accompanied by applying pressure on the wafer using a steel press.

However, the sintering method is not cited in this document as one of several methods which are all held as advantageous, so that it would be possible to demonstrate that they were not.

In tests, it was, in fact, possible to identify several shortcomings of this prior art technique. The first shortcoming is that the semiconductor material is a powdered polycrystal such as mercury iodide $HgI_2$ and that it has been pre-treated to attain a high degree of purity. This results in a source of additional costs in that the powder used at the beginning of the wafer manufacturing process must first be submitted to a purification process.

A second shortcoming of this prior art technique is that one of the materials proposed (in this case, gold) for the electrodes—which make it possible to recover the electrical charges produced during the X-photon conversion in the semiconductor material for the wafer thus sintered—is a metal which chemically reacts during hot sintering of the powdered semiconductor material, in this case $HgI_2$. This results in degradation and even a local destruction of the electrode(s).

This invention aims to solve these problems and shortcomings of the prior art.

BRIEF SUMMARY OF THE INVENTION

For this purpose, the invention proposes a manufacturing method for a semiconductor wafer for a direct conversion X-ray detector. This method comprises a step for applying pressure to a powdered polycrystalline semiconductor material and a step for heating during a set time period. In accordance with the invention, the impurity rate of the polycrystalline semiconductor material is at least 0.2%.

According to other characteristics of the method:
The pressurizing step consists of applying an axial compression force to the powdered polycrystalline semiconductor material of a value which will ensure an axial orientation C of the polycrystalline semiconductor material grains according to the direction of the application C of said axial compression force;
The value of said axial compression force is comprised of between 100 MPa and 1,000 MPa, and in that the duration of the hot pressing is equal to at least one hour;
The temperature of the heat is comprised between 70° C. and 200° C., and the duration of the heating is equal to at least one hour;
The step of applying pressure is implemented upon starting the heating step;
The step of applying pressure is implemented throughout the entire heating step;
The powdered semiconductor material comprises at least one of the constituents chosen from among: $PbI_2$, $HgI_2$, PbO;
The step of applying pressure is preceded by a step in which a dopant is incorporated into the polycrystalline semiconductor material. The dopant is preferably chosen for $HgI_2$ or $PbI_2$ from among halogenated compounds, and especially chosen from among CsI, $CdI_2$, $SnCl_2$, AgI or $BiI_3$ and, for PbO, chosen from among the oxide compounds.

The invention also proposes a direct conversion X-ray detector that comprises a semiconductor wafer manufactured in accordance with the invention.

In accordance with other characteristics of said detector:

It is associated with an integrated semiconductor circuit, and it comprises a first continuous electrode in contact with an entry surface of the wafer, and a second electrode constituted by a plurality of conductive patches in contact with the opposite surface of the wafer, so as to provide a one-dimensional or two dimensional array of pixels, said first and second electrodes being electrically connected with the integrated semiconductor circuit associated with a surface upon which the semiconductor wafer has been deposited, the integrated semiconductor circuit being arranged so that it produces a plurality of electrical signals representative of the intensity of the X-rays received in the different pixels of said semiconductor chip.

The invention further provides for an apparatus for X-rays, including dental X-rays, using at least one direct conversion X-ray detector according to the invention.

Such an apparatus:

Comprises at least one direct conversion X-ray detector in accordance with the invention, and it further comprises at least one controlled X-ray source and a control circuit to execute at least one X-ray exposure in the direction of said at least one direct conversion X-ray detector and for deducing therefrom, by viewing, printing and/or recording at least one graphical representation based on the plurality of electrical signals generated by said at least one direct conversion X-ray detector.

It is an intraoral or extraoral dental X-ray apparatus.

BRIEF DESCRIPTION OF THE FIGURES

Other characteristics and advantages of this invention will be better understood using the description and the accompanying drawings in which.

According to the invention, the manufacturing method uses a powdered semiconductor material.

According to the scientific literature, $PbI_2$, $HgI_2$ and/or PbO based materials are potentially the most effective. In one preferred embodiment, the material chosen is $HgI_2$. Furthermore, when the material possesses an anisotropic electric mobility which is the case with the aforementioned materials, it is preferable that it be shaped so that the electric current flows in the direction of greater mobility.

In the prior art, as was described above, the powders used to create a detection chip by sintering must be subjected to a series of purification steps to use the most pure semiconductor material possible.

On the contrary and surprisingly, the inventors have observed that the presence of a minimum level of impurities makes it possible to obtain a much higher yield of electrical conversion of X-photons.

The inventors find that, in the case of an $HgI_2$ wafer manufactured from a less pure powder, better results are obtained in terms of detection sensitivity.

The desirable and admissible impurities in accordance with the invention are in particular, metal waste products contained in the initial powder or those that come from tools used to reduce the powder and to measure or calibrate the average diameter of the particles of the powder and from the manufacturing process of the industrial powder producer.

Preferably, the powdered semiconductor material to be used to create the sintering of the chip should be 99.0% pure, with a rate of impurities, especially metals, lower than 1.0%.

Such a "non-purified" powder is advantageously commercially available, thus allowing one to remove all the costs involved in a series of purification steps. Specifically, manufacturers of powders commercially offer gradations of purity in their products by groups of ten. Tests conducted by the inventors showed improved results in the sintered powders for direct X-photon conversion from the group of ten corresponding to 0.2% impurities. This represents a gain of more than two thousand times the impurity required in the prior art including the aforementioned document U.S. Pat. No. 5,892,227.

The inventors then realized that the application of an axial compressive load to such a material having a predetermined minimum rate of impurities which also favors an improvement in the yield of the electrical conversion by reorienting the grains along a crystallographic axis C common to the grains making up the initial powder. This characteristic is combined with the minimal impurity rate characteristic in a preferred embodiment.

Figure 1:
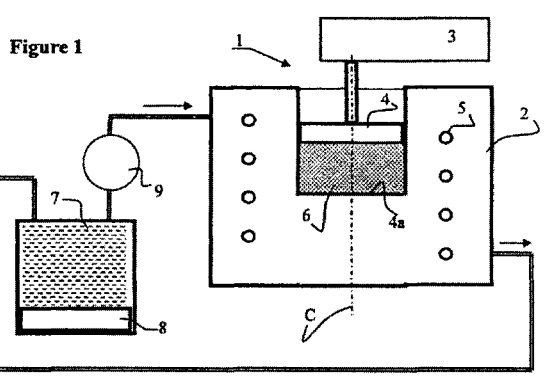
FIG. 1 shows a schematic representation of a device with which certain steps of the method in accordance with the invention may be implemented.

In FIG. 1, a device which makes it possible to implement the manufacturing method is shown.

A furnace 1 is made up by a heat conducting body 2, which has a central opening 6 limited by a lower wall 4a and by an axial compression press 4 placed above the powdered semiconductor material to be sintered.

A mold whose cavity has the shape to be taken by the semiconductor wafer material is placed in the central opening of the housing 6 or furnace 1.

For example, this mold makes it possible to produce a wafer with at least two opposing and parallel surfaces and with a circular or rectangular shape.

The heat conducting body 2 is pierced by channels 5 for circulation of a heated oil from a reserve 7. The reserve oil is heated by an electric resistor 8 connected by a circuit controlling the duration and/or the temperature for sintering (not shown).

The heated oil is aspirated by an electric pump 9 controlled by the control circuit for the duration and/or the temperature for sintering (not shown). The hot oil enters into the channels 5 of the body 2. These channels are connected in a spiral shape and the flow of the heating oil is then routed towards the reserve 7.

Preferably, the upper press 4 is activated by a mechanism 3 which regulates the value, and the duration of the application, of the force of the axial compression applied to the powder, then to the semiconductor wafer housed in the chamber 6 of the furnace 1.

This implementation of the axial compression is preferably performed upon startup of the heating, i.e., of the heating for sintering the powder and then the wafer being manufactured.

In another embodiment, interesting results were also obtained by performing cold axial compression, which is carried out before activating the heating for the manufacture by sintering of the wafer made of semiconductor material. In particular, good results were obtained by performing shell-firing after prior cold axial compression for up to an hour.

Figure 2A:
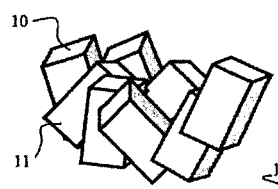
FIGS. 2a and 2b are diagrams explaining the effect resulting from the axial compression.

FIG. 2a is a schematic illustration of the grains in a wafer made of semiconductor material. These grains—shown, for example, by the grains 10, 11—have a parallelepiped form. This form does not predetermine the actual shape of the grains in the pellet, but its purpose is to highlight the anisotropy of their electrical properties, in the case of an anisotropic material. The direction C of greater electrical mobility corresponds to the smallest dimension of the parallelepiped.

The grains shown in FIG. 2a are oriented in any direction. As a result, if electrical charges flow through the material, they will cross the grains according to their direction of greater electric mobility, and will then travel to other grains in a lower electric mobility direction. This will result in the overall electrical mobility of the material not being maximized.

Figure 2B:
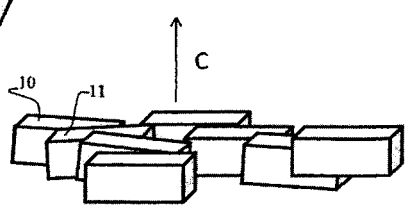

In FIG. 2b, for implementation of axial compression in a given direction C, the grain surfaces 10, 11 of the particle in the powdered semiconductor material tends to virtually align such that direction C of the higher electrical mobility is parallel to the axis of the axial compression.

The overall electric mobility of the ceramic is increased along this direction. This results in an improved flow of electrical charges along this direction, and hence an improved yield in the electrical conversion of X-photons.

The compression, or application of pressure, or sintering under pressure of the powder to be sintered has already been practiced in the prior art. But in particular, it is noted that the desired effect was then a simple compaction of the powder to impart better mechanical strength before the pellet thus "pre-compacted" is placed in the sintering furnace. In particular, the compaction only results in a reduction in the powder volume, the voids between the powder particles being reduced by applying this pressure.

According to the invention, applying the axial compression at the same time as heating exceeds that single state of volume reduction to promote the growth of grains having the orientation of the axis C parallel to the axis of compression at the expense of the other grains and results in a semiconductor chip having a preferred orientation of the grains.

The compression performed in the manufacturing method according to the invention should preferably take place at the beginning of the heating step. It occurs with a compression load or force at a set value, during a set time period, and at a set temperature value.

After the finishing the axial compression step, the heating step for sintering can be stopped immediately or may be continued for a set time period or at a maintained temperature or at another predetermined temperature, in particular according to the gradation of the powdered semiconductor material and/or the thickness of the wafer that one wishes to produce.

Good results were also obtained by first practicing an axial cold compression step, and by performing it just after the sintering heating step itself. In such an embodiment, it was found advantageous to use a technique of shell-firing; the axially compressed pellet is placed on a layer of non-compacted powder and finally covered with a layer of non-compacted powder.

The heating step makes it possible for the grains to grow within the wafer. The presence of the powder bed during sintering can limit contact between the wafer and the atmosphere during sintering. The phenomena of transport of matter on the surface are limited by the gradual evaporation and recondensation of the material on the surface.

Shell-firing makes it possible to obtain a better surface, i.e., better flatness by reducing roughness from the surfaces of the opposing sides of the wafer. Shell-firing also makes it possible to reduce the formation of a surface parasite phase which may occur if the wafer had been directly in contact with the furnace atmosphere during annealing.

The surfaces of the press 4 and the bottom of the mold 4a have surface states which make it possible to comply with a smooth surface state free of open surface porosity that was possible to obtain with axial compression and heating during the sintering itself.

It is thus perfectly possible to directly make an electrode deposit on the two "active" surfaces opposing the wafer made of semiconductor material and to deposit the assembly directly, of the electrodes and of the wafer, on an integrated CMOS circuit, which will be described later.

In one particular embodiment, the axial compression step is preceded by a step during which a dopant is incorporated in the semiconductor material. In one preferred embodiment, the dopant is chosen from among iodide compounds and is for example, CsI or $BiI_3$.

Figure 3:
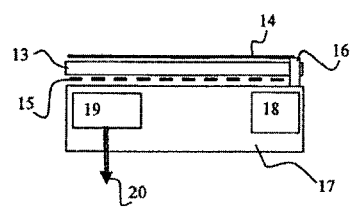
FIG. 3 is a schematic representation of a direct conversion X-ray detector using a semiconductor wafer manufactured in accordance with the invention.

In FIG. 3, a direct conversion X-ray detector is illustrated which is produced by using a ceramic or semiconductor material wafer 13 obtained with the manufacturing method of the invention. The wafer made of a semi-conductor material 13 has two parallel and opposing surfaces, one lower and one upper when viewing FIG. 3. They have a surface state which is perfectly flat and free of roughness.

It is then possible to deposit one or more metal layers, such as palladium, by evaporation, or by means of any suitable technique, which will constitute respectively a first electrode 14 on the upper surface and a second electrode 15 on the lower surface of the wafer made of semiconductor material.

In one preferred embodiment, the first electrode 14 is a continuous, flat and two dimensional, which may be crossed by the incident X-photon flow. Depending on the energy of the incident X-photons, and the wavelength, the axial thickness separating the upper surface of the lower surface of the wafer 13 is determined by maximizing the absorption of the X-photons through the second electrode 15.

This second electrode 15 is not produced in a two dimensional continuous fashion, but rather in the form of patches defining the right to a pixel image sensor for each patch.

Depending on the case, the second electrode 15 is then configured in such a way that the conductor patches are arranged:

in one linear direction or another, but one dimensional, to create a one dimensional image sensor;
or in two dimensions, under various arrangements chosen during the design of the detector, to create a two-dimensional sensor for a 2D image.

Each conductive patch on the second electrode is then connected by a network of conductive lines to a set of amplifiers for signals detected for each pixel. As is known, the 2D pixel arrangement thus formed can be operated directly or by multiplexing, including a 2D addressing mechanism in rows and columns. To this end, the direct conversion detector of the invention also comprises a integrated CMOS circuit 17, upon which the upper surface of the wafer made of semiconductor material 13, with its electrodes 14 and 15, is deposited and fixed.

The integrated CMOS circuit 17 is mainly comprised of a detection circuit 18 and a signal processing circuit 19. The circuit 18 is connected to each electrical charge pixel sensor. Each pixel sensor comprises a preamplifier and a formatting circuit responsive to the charge produced on each pixel of the wafer 13. The circuit 19 is provided with means for producing electrical signals representative of the X-ray intensity received in the various pixels of the semiconductor chip.

For this purpose, the electrodes 14 and 15 of the semiconductor chip 13 are electrically connected to the conductive input patches (not shown) of the integrated CMOS circuit 17 by electrical connections. The conductive input patches of the integrated CMOS circuit 17 are electrical connected to the properly polarized sensor circuits 18 as is known.

Not all the necessary circuits to be developed for the integrated CMOS circuits 17 are described herein, but only those necessary so that the invention may be understood. The electrical signals representative of the of the received X-ray intensity produced by the circuits 18 are available on the output terminals 20 of the integrated complex circuit 13-20 thus formed which constitute a direct conversion X-ray detector.

Figure 4:
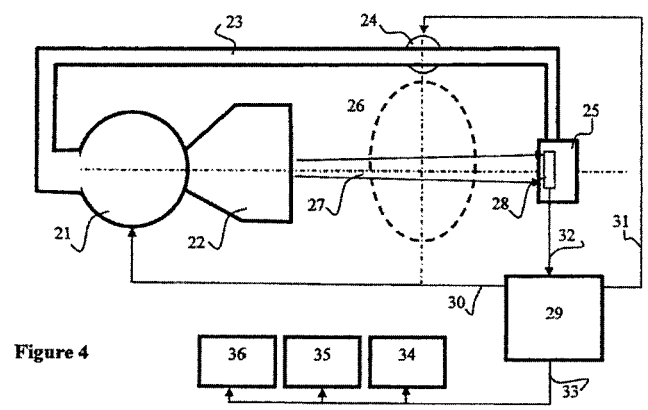
FIG. 4 is a diagram of a particular embodiment of a dental X-ray apparatus using a direct conversion X-ray detector in accordance with the invention.

In FIG. 4, a dental X-ray apparatus is schematically shown that advantageously uses at least one direct conversion X-ray detector as described in reference to FIG. 3.

The sensor equipped with the wafer of the invention can be used in an extraoral dental imaging system. One source 21 of X-rays is mounted on a mobile arm 23 on a support 24 upon which it can be moved. With regard to the X-ray source 21, the arm 23 carries an apparatus 25 designed to produce at least one image signal produced by using at least one sensor with a direct conversion X-ray detector 28 constituted in accordance with that described above.

The sensor equipped with the wafer of the invention can be used in an intraoral dental imaging system. The sensor is then positioned inside the patient's mouth behind the tooth to be X-rayed. The X-ray source is positioned on the adjustable arm. It is positioned against the patient's cheek just before exposure.

The direct conversion X-ray detector 28 is opposite the X-ray source 21 equipped with an assembly 22 providing filtering and collimating of the incident X-rays. X-rays 27 then pass through an analysis region 26 such as the head of a patient, or a part of his jaw, to be examined by involving the direct conversion 28 X-ray detector 27.

The dental radiology apparatus thus constituted also comprises a calculator 29 for performing such a control circuit 29, 31 to perform at least one X-ray exposure. The calculator 29 mainly comprises:
means for generating control signals 30 from the X-ray source 21 and the filter and collimation unit 22;
means for generating control signals 31 for activating the arm 23, as desired, so as to perform determined scans of the region to be analyzed 26 in synchronism with the X-ray exposures determined by the X-ray source 21;
means for receiving and processing various electric signals 32 representative of the intensity of X-rays received in the various pixels of the semiconductor sensor chip direct conversion of X-rays 28;
means to derive by viewing, printing and/or recording at least one graphic representation on the basis of the plurality of electrical signals generated by said at least one direct conversion X-ray detector.

These last means of calculating 29 and are connected to a graphic display device 34, a graphics printer 35 and/or a storage system 36 and direct consultation or by means of a communication network.

We noted that this type of radiology apparatus operates with a recurrence of high frequency that require the performance that the wafer made of semiconductor material obtained by the manufacturing method of the invention which makes it possible to attain what we shall show in a later section.

EXAMPLES

Example 1

For the polycrystalline semiconductor materials, the following parameters are used:
Sintering temperature: 100° C.
Axial compression load: 300 Mega ($3.10^8$) Pascals.
Duration of pressurizing at this temperature: 20 hours.

Example 2

For the polycrystalline semiconductor materials, the following parameters are used:
Sintering temperature: Comprised between 70° C. and 130° C.
Axial compression load: Comprised between 100 Mega Pascals and 800 Mega Pascals.
Duration of pressurizing at this temperature: At least 1 hour.

Example 3

For mercury iodide $HgI_2$, the following parameters are used: Sintering temperature: Lower than 200° C.
Axial compression load: Lower than 1000 Mega Pascals.
Duration of pressurizing at this temperature: At least 1 hour.

Example 4

For mercury iodide $HgI_2$, the following parameters are used:
Sintering temperature: Comprised between 70° C. and 200° C.
Axial compression load: Comprised between 100 and 1000 Mega Pascals.
Duration of pressurizing at this temperature: At least 1 hour.

Example 5

For semiconductor materials selected from $PbI_2$, $HgI_2$ a dopant of a halogenated compound was added selected from CsI, $BiI_3$, $CdI_2$, $SnCl_2$ and AgI. For semiconductor materials such as PbO, doping was performed by adding an oxide compound.

The concentration indicated is on the order of a few percentages.
Testing the Wafers and Direct Conversion Detectors
Effects of the Purity of the Starting Powder on the Sensitivity of the X-Ray Detection.

In a series of tests, the powder used to make the ceramics was a commercial powder sold by the company "Sigma Aldrich" with a purity equal to 99.0% (reference 221090 ACS reagent, ≥99.0%).

For comparison, wafers were also created using a commercial powder with a purity of 99.999% (supplier reference 203785, 99.999% trace metal basis).

Table 1 below shows the measurements of the dark current and the sensitivity for the wafers made with powder having a purity of 99.0% and 99.999%. For physical reasons, it is not possible to know the exact X-ray dose received by the sample. Only the dose emitted by the source can be known. However, sensitivity measurements performed for two samples of the same size and thickness are comparable. Therefore, we compared the relative sensitivity of a sample in relation to the other one.

TABLE 1

Purity Study

| | Dark Current (nA/cm$^2$) | Relative Sensitivity |
|---|---|---|
| Purity 99.0% | 251.6 (±25%) | 3.94 |
| Purity 99.999% | 215.9 (±19%) | 1.0 |

The dark current must be as weak as possible to have the best signal to noise ratio. Sensitivity refers to the number of loads collected based on the X-ray dose and the electrode surface. Maximizing this quantity is the goal.

Wafers made from the 99.0% pure powder, i.e., with a "poor" purity with a dark current equivalent to the wafers prepared with a very pure powder, and especially with a greater sensitivity.

Crystallographic Analysis

Crystallographic analysis has shown that the method according to the invention has the effect of promoting grain growth and resorption of the porosity. The grains are not just welded to each other. The smaller grains are more "absorbed" by the larger ones. This growth of the larger grains at the expense of the smaller grains occurs in any sintering operation, but the method according to the invention makes it possible to increase its efficiency due to the applied load.

Consequently, the polycrystalline material thus obtained has a porosity that is much lower than the material obtained by simple sintering without pressure or by the simple application of pressure without sintering.

Second, when the grains have an anisotropic crystalline structure, maintaining an axial compression or load during sintering can promote the growth of the grains having a minimal mechanical energy and thus making it possible to obtain a polycrystalline material in which the grains are in the preferred orientation.

In the case of HgI$_2$, this makes it possible to obtain a material having an orientation such that the direction of greater electrical conductivity is parallel to the axis of pressure. The lower porosity and the preferential orientation of the grains produced by sintering under pressure makes it possible to improve the electrical transport properties in comparison with a simple sintering or compaction without sintering.

Third, placing the wafer under pressure, by avoiding evaporation, makes it possible to obtain a better evenness and less surface roughness of the polycrystalline material, which subsequently allows better contact between the electrodes and the surfaces of the material, and to decrease defects on the surface of the material that could degrade the efficiency of the electrical charge collection.

Micro-Structural Study

Comparing the microstructure of various wafers made of semiconductor material to derive the benefit of the orientation by axial compression. The HgI$_2$ powder, a sintered wafer, and a wafer sintered under pressure are compared. The preferred orientation of the grains in a wafer sintered under pressure and a powder to be analyzed by X-line diffraction. To compare the proportion of a structure oriented along the crystallographic axis C, the area under the diffraction lines characteristic of the crystallographic axis was measured under the diffraction lines characteristic of this crystallographic axis (type (00x) lines, where x is a nonzero positive integer). Table 2 below shows the results for an HgI$_2$ powder, a sintered wafer from the prior art, and a wafer sintered under pressure in accordance with the invention. The relative intensity is calculated as the ratio between the measurement line (type (00x)) to a reference line (line (102)).

TABLE 2

Intensity relative to the characteristic lines of the axis C

| Relative intensity | Powder | Sintered | Sintered under pressure |
|---|---|---|---|
| Reference Line (102) | 1 | 1 | 1 |
| Line (002) | 0.27 | 1.52 | 5.18 |
| Line (004) | 0.22 | 1.23 | 3.13 |
| Line (006) | 0.06 | 1.37 | 1.57 |

In the case of the ceramic or sintered wafer made under pressure according to the invention, one obtains the greatest values for the characteristic lines for the crystallographic axis C, i.e., of the type (00x) (2a and 2b). There is therefore a preferential orientation which is the most important according to this axis.

Return to Equilibrium Time after an X-Ray Pulse ("Lag")

As was disclosed in the description of FIG. 4, of significant importance in the case of an imaging pulse detector, for example, in 3D imaging is the time to return to equilibrium or "lag", i.e., the time required for the current produced by an X-ray pulse to return to zero after the end of the pulse. To be able to produce rapid images, this "lag" must be as short as possible.

The "lag" on the semiconductor wafers produced according to the invention, as well as references: The CdTe monocrystal and HgI$_2$ monocrystal to be measured. Table 3 below shows the results.

TABLE 3

Lag Measurement

| | HgI$_2$ Wafers | CdTe Monocrystal | HgI$_2$ Monocrystal |
|---|---|---|---|
| Lag | 1 ms | 66 ms | 15 ms |

The HgI$_2$ wafers produced by axial sintering under pressure according to the manufacturing method in accordance with the invention exhibit the lowest "lag".

Linearity in Time.

Another performance criterion is the linearity of the direct conversion X-ray detector over time.

The electric charge collected by the semiconductor chip must be proportional to the dose of X-rays received. The linearity of the wafers was measured by subjecting them to a series of X-rays, i.e., a series of X-ray exposures with interposed pauses. We measured the amount of charges collected by the wafer made of semiconductor material, the cumulative quantity over time, by exposing the direct conversion X-ray detector, the X-ray wave stream, composed of a sequence of pulses. The characteristics of the X-ray wave stream process were:

Duration of a pulse: 50 Ms.

Duration of the following dark current: 50 Ms.

The accumulation of charges collected CCC versus time complies with high precision for a linear relationship during the exposure time interval [0.28 s] of the direct conversion X-ray detector:

CCC=a*t, with a=35000/28 in units of charges collected per unit of time (in seconds).

The amount of accumulated collected charges CCC increases from a value of zero before exposition to the X-ray wave stream begins in a linear fashion over time. This is an advantage for use in 3D imaging, that is to say, all the X-ray exposures performed make it possible to collect the same number of charges.

Production of a Direct Conversion X-Ray Detector

The thickness of the wafer made from semiconductor material produced by the method of the invention depends on the particle size of the starting powder and the value of the applied compressive force.

In one example of an embodiment of a direct conversion X-ray detector, a density which was very close to that of a $HgI_2$ monocrystal (98%) was attained.

The amount of powder was determined by the ratio: Powder mass=section×thickness×density (with a density of 6.36 g/cm$^3$).

In this embodiment, it was not necessary to make a preform. The mold placed in the furnace (FIG. 1) was used during the sintering under pressure to give the final shape to the wafer manufactured in accordance with the invention.

It was noted that the longer the sintering is, the greater the density and the larger the size of the grains will be.

The wafer exits the furnace in a cylindrical form. It was cut and trimmed to form a rectangular parallelepiped with dimensions of 15 cm×15 cm×500 µm (thickness). The direct conversion X-ray detector was produced by evaporating two conductive electrodes of 50 nm on the two opposing faces of the wafer whose surface state was previously cleaned properly and the unit was deposited on an integrated CMOS circuit as was described using FIG. 3.

The invention claimed is:

1. Method of manufacturing a direct conversion X-ray detecting semiconductor chip for a direct conversion X-ray detector, the method comprises a step for applying pressure (3, 4, 4*a*) to a powdered polycrystalline semiconductor material and a step for heating (5-9) the powdered polycrystalline semiconductor material during a set time period, where the purity of the powdered polycrystalline semiconductor material is equal to or greater than 98% and less than 99.8%.

2. Method according to claim 1, characterized in that the step for applying pressure consists of applying (3) an axial compression force (4, 4*a*) to the powdered polycrystalline semiconductor material of a value which will ensure an axial orientation (C) of the polycrystalline semiconductor material grains according to the direction of the application (C) of said axial compression force.

3. Method according to claim 2, characterized in that the value of said axial compression force is comprised between 100 and 1,000 MPa, and in that the duration of the pressurizing is equal to at least an hour.

4. Method according to claim 3, characterized in that the temperature of the heat is comprised between 70° C. and 200° C., and in that the duration of the heating is equal to at least one hour.

5. Method according to claim 1, characterized in that the step of applying pressure is implemented upon starting the heating step.

6. Method according to claim 5, characterized in that the step of applying pressure is implemented throughout the entire heating step.

7. Method according to claim 1, characterized in that the powdered semiconductor material comprises at least one of the constituents chosen from among: $PbI_2$, $HgI_2$, PbO.

8. Method according to claim 1, characterized in that the step for applying pressure is preceded by a step in which a dopant is incorporated into the polycrystalline semiconductor material, the dopant being preferably selected for $HgI_2$ or $PbI_2$ from halogenated compounds, and especially selected from among: CsI, $CdI_2$, $SnCl_2$, AgI or $BiI_3$, and for PbO selected from oxide compounds.

9. Direct conversion X-ray detector, characterized in that the direct conversion X-ray detector comprises a semiconductor wafer (13) manufactured in accordance with claim 1.

10. Direct conversion X-ray detector according to claim 9, characterized in that the direct conversion X-ray detector is associated with an integrated semiconductor circuit, and in that the integrated semiconductor circuit comprises a first continuous electrode (14) in contact with an entry surface of the wafer (13), and a second electrode (15) constituted by a plurality of conductive patches in contact with the opposite surface of the wafer (13), so as to provide a one-dimensional or two dimensional array of pixels, said first and second electrodes being electrically (16) connected with the integrated semiconductor circuit (17) associated with a surface upon which the semiconductor wafer (13) has been deposited, the integrated semiconductor circuit (17) being arranged (18, 19) so that the integrated semiconductor circuit produces a plurality of electrical signals (20) representative of the intensity of the X-rays received in the different pixels of said semiconductor chip.

11. Radiological apparatus, in particular, for dental radiology, using at least one direct conversion X-ray detector according to claim 10, characterized in that the dental radiological apparatus further comprises at least one controlled X-ray source (21,22) and a control circuit (29, 30) to execute at least one X-ray exposure in the direction of said at least one direct conversion X-ray detector (28) and for deducing (33) therefrom, by viewing (34), printing (35) and/or recording (36) at least one graphical representation based on the plurality of electrical signals generated by said at least one direct conversion X-ray detector (28).

12. Radiological apparatus in accordance with claim 11, characterized in that said apparatus is an intraoral dental X-ray apparatus or an extraoral dental X-ray apparatus.

13. Method according to claim 1, further comprising:
produinc a semiconductor wafer made of only the powdered polycrystalline semiconductor material, and
depositing an electrode on a surface of the semiconductor wafer, wherein the producing a semiconductor wafer comprises applying pressure between 100 and 1,000 MPa to only the powdered polycrystalline semiconductor material while heating with a temperature between 70° C. and 200° C. during a set time period.

* * * * *